United States Patent
Jurcik, Jr. et al.

(10) Patent No.: US 8,758,867 B2
(45) Date of Patent: Jun. 24, 2014

(54) NEUTRAL LIGAND CONTAINING PRECURSORS AND METHODS FOR DEPOSITION OF A METAL CONTAINING FILM

(75) Inventors: Benjamin J. Jurcik, Jr., Tsukuba (JP); Christian Dussarrat, Wilmington, DE (US)

(73) Assignee: L'Air Liquide, Société Anonyme pour l'Etude et l'Exploitation des Procédés George Claude, Paris (FR)

( * ) Notice: Subject to any disclaimer, the term of this patent is extended or adjusted under 35 U.S.C. 154(b) by 1325 days.

(21) Appl. No.: 12/212,500

(22) Filed: Sep. 17, 2008

(65) Prior Publication Data

US 2009/0104375 A1    Apr. 23, 2009

Related U.S. Application Data

(60) Provisional application No. 60/973,092, filed on Sep. 17, 2007.

(51) Int. Cl.
*C23C 16/513* (2006.01)

(52) U.S. Cl.
USPC .......................................... 427/576; 427/252

(58) Field of Classification Search
USPC ................................. 427/576, 252
See application file for complete search history.

(56) References Cited

U.S. PATENT DOCUMENTS

| | | | |
|---|---|---|---|
| 4,425,281 A | 1/1984 | Doyle | |
| 5,098,516 A * | 3/1992 | Norman et al. | 216/78 |
| 5,441,766 A | 8/1995 | Choi et al. | |
| 5,767,301 A | 6/1998 | Senzaki et al. | |
| 7,138,336 B2 * | 11/2006 | Lee et al. | 438/680 |
| 7,220,671 B2 * | 5/2007 | Simka et al. | 438/680 |
| 7,311,946 B2 * | 12/2007 | Garg et al. | 427/404 |
| 2006/0121709 A1 | 6/2006 | Doppelt | |

FOREIGN PATENT DOCUMENTS

| | | |
|---|---|---|
| EP | 0 533 070 | 3/1993 |
| WO | WO 92 17971 | 5/1992 |
| WO | WO 00 17278 | 3/2000 |
| WO | WO 2004 036624 | 4/2004 |

OTHER PUBLICATIONS

International Search Report for PCT/US2008/076732.
Thompson, et al. "Copper(I) complexes with bis(trimethylsilyl)acetylene: Role of ancillary ligands in determining π back-bonding interactions." Organometallics, vol. 25, No. 11, May 22, 2006, pp. 2712-2714.
Dubois, et al. "Selectivity and copper chemical vapor deposition." J. Electrochem. Soc., vol. 139, No. 11, Nov. 1992, pp. 3295-3299.
Donnelly, et al. "Copper metalorganic chemical vapor deposition reactions of hexafluoroacetylacetonate Cu(I) vinyltrimethylsilane and bis(hexafluoroacetylacetonate) Cu(II) adsorbed on titanium nitride." J. Vac. Sci. Technol. A 11(1) Jan.-Feb. 1993, pp. 66-77.
Chi, et al. "Chemistry of copper(I) B-diketonate complexes." J. of Organometallic Chemistry, 449 (1993) pp. 181-189, XP002229352.
Choi et al. "Copper(I) test-butyl 3-oxobutanoate complexes as precursors for chemical vapor deposition of copper." Beckman Institute of Advanced Science and Technology, U. of Illinois at Urbana, vol. 10, No. 9, pp. 2326-2328. 1998.
Hakansson, et al. "Copper(I) complexes with conjugated dienes." J. of Organometallic Chemistry (2000), 602(1-2), 5-14, 2000, XP004200823.
"Acetylacetone," http://en.wikipedia.org/wiki/Acetylacetone, 5 pages, accessed Nov. 4, 2012.
Hampden-Smith, M.J. et al., "Chemical vapour deposition of copper from (hfac)CuL compounds," Polyhedron, vol. 14, No. 6, 1995, pp. 699-732.
"Hexafluoroacetylacetone," http://en.wikipedia.org/wiki/Hexafluoroacetylacetone, 2 pages, accessed Nov. 4, 2012.

* cited by examiner

*Primary Examiner* — Jie Yang
(74) *Attorney, Agent, or Firm* — Patricia E. McQueeney

(57) ABSTRACT

Methods and compositions for depositing metal films are described herein. In general, the disclosed methods utilize precursor compounds comprising gold, silver or copper. More specifically, the disclosed precursor compounds utilize neutral ligands derived from ethylene or acetylene.

13 Claims, No Drawings

NEUTRAL LIGAND CONTAINING PRECURSORS AND METHODS FOR DEPOSITION OF A METAL CONTAINING FILM

CROSS REFERENCE TO RELATED APPLICATIONS

The present application claims the benefit of U.S. Provisional Application Ser. No. 60/973,092 filed Sep. 17, 2007, herein incorporated by reference in its entirety for all purposes.

BACKGROUND

1. Field of the Invention

This invention relates generally the deposition of thin films, as used in the manufacture of semiconductor, photovoltaic or TFT-LCD devices. More specifically, the invention relates to compositions and methods for depositing a copper, silver or gold containing precursors.

2. Background of the Invention

ALD (Atomic Layer Deposition) and CVD (Chemical Vapor Deposition) are particularly useful techniques for deposition of metal films as compared to other methods of deposition such as physical vapor deposition (PVD) methods like sputtering, molecular beam epitaxy, and ion beam implantation. ALD and CVD can also be used to provide flexibility in the design of manufacturing electronic devices including the potential to reduce the number of processing phases required to provide a desired product. These techniques allow conformal deposition, selective deposition for the deposition of copper, silver, gold and other materials. Suitable processes to form metal films require the identification of relevant precursors requiring strict requirements such as being thermally stable, easily vaporized, reactive, with clean decomposition.

The need for high performance interconnection materials increases as device feature sizes shrink and device density increases. Copper provides an alternative to CVD of aluminum in ultra large scale integrated (ULSI) devices due to its low resistivity (1.67 μΩcm for Cu, 2.65 μΩcm for Al), high electromigration resistance and high melting point (1083° C. for Cu, 660° C. for Al). Its low interconnect resistivity also may allow for faster devices.

Copper precursors are quite volatile and show low deposition temperatures, but are highly, sensitive to heat and oxygen. The latter precursors are rather stable, but are isolated as solids with high melting points and thus require high deposition temperatures. It is common for impurities such as carbon or oxygen to be incorporated during the thermal CVD process when using certain organometallic precursors. For instance, (η5-C 5H 5)Cu(PMe3) produces copper films leading to incorporation of phosphorus. Moreover, phosphine-containing molecules are disqualified because of their high toxicity. Organic phosphines are very hazardous and PF3 being both hazardous and might lead to undesired phosphorus contamination and fluorine-induced etching/damage. Such chemicals might therefore be subject to strict regulations.

An example of an existing copper precursor includes (1,1,1,5,5,5-hexafluoro-2,4-pentanedionate)CuL ((hfac)CuL), where L is a Lewis base. These types of precursors have been the most studied copper precursors to date because they can deposit copper via a thermal disproportionation reaction. Especially (1,1,1,5,5,5-hexafluoro-2,4-pentanedionate)Cu (trimethylvinylsilane), which has attracted much attention because it is a liquid with reasonably high vapor pressure. Other copper compounds such as (1,1,1,5,5,5-hexafluoro-2,4-pentanedionate)CuL, where L is 1,5-cyclooctadiene (CUD), alkyne or trialkylphosphine, are either solids or liquids with a low vapor pressure. Although (hfac)Cu(trimethylvinylsilane) ((hfac)Cu(tmvs)) has been the most utilized copper precursor, its stability is not satisfactory for the selective growth of copper films with reproducibility. In addition, studies have demonstrated that the chemical vapor deposition reaction of (hfac)Cu(tmvs) under ultra high vacuum conditions produced contamination by carbon and fluorine in the deposited films. Therefore, a precursor with high volatility and stability, which contains no fluorinated ligands, is more desirable for the deposition of copper by CVD.

Copper compounds of acetoacetate derivatives which contain no fluorinated ligands have been previously used as CVD precursors. Although these compounds were reported to be volatile and capable of depositing copper films at low substrate temperatures. The studied acetoacetate derivatives were found to be attractive since they were volatile without employing fluorinated ligands and deposited copper films at temperatures below 200° C. However, these derivatives are solid with high melting points and are incapable of selective deposition of copper. On the other hand, the Cu(I) acetoacetate derivatives deposited copper films at relatively low temperatures via disproportionation reaction. However, few are practical for use as CVD precursors since they are either solids or liquids with a low vapor pressure or they have an extremely low thermal stability (i.e. their decomposition temperature is within a few degrees of their vaporization temperature).

Consequently, there exists a need for alternate precursors for deposition of copper, silver, or gold containing films.

SUMMARY

The invention provided novel methods and compositions for the deposition of a metal containing film. In general, the disclosed compounds utilizing precursor compounds comprising copper, gold, silver, etc.

In an embodiment, a method for depositing a metal containing film onto one or more substrates comprises providing at least one substrate into a reactor. At least one metal containing precursor is introduced into the reactor, wherein the metal containing precursor has the general formula:

M is one of copper, silver or gold. R, R', and R" are selected from hydrogen, a C1-C6 linear, branched or cyclic alkyl group, NO2, SiR$^1$R$^2$R$^3$; and GeR$^1$R$^2$R$^3$. R$^1$, R$^2$, R$^3$ are independently selected from hydrogen, and a C1-C6 linear, branched or cyclic alkyl group. L is a neutral ligand derived from ethylene or acetylene. At least part of the metal containing precursor is deposited onto one or more of the substrates to form either a pure metal film, or an alloy film.

In another embodiment, a method for depositing a metal containing film onto one or more substrates comprises providing at least one substrate into a reactor. At least one metal containing precursor is introduced into the reactor, wherein the metal containing precursor has the general formula:

M is one of copper, silver or gold. R, R', and R" are selected from hydrogen, a C1-C6 linear, branched or cyclic alkyl group, NO2, $SiR^1R^2R^3$; and $GeR^1R^2R^3$. $R^1$, $R^2$, $R^3$ are independently selected from hydrogen, and a C1-C6 linear, branched or cyclic alkyl group. L is a neutral ligand derived from ethylene or acetylene. A plasma source is provided, and sequentially activated/deactivated after the introduction of the metal containing precursor. At least part of the metal containing precursor is deposited onto one or more of the substrates to form either a pure metal film, or an alloy film.

In another embodiment, a composition comprises a precursor with the general formula:

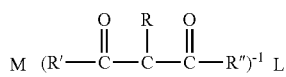

M is one of copper, silver or gold. R, R', and R" are selected from hydrogen, a C1-C6 linear, branched or cyclic alkyl group, NO2, $SiR^1R^2R^3$; and $GeR^1R^2R^3$. $R^1$, $R^2$, $R^3$ are independently selected from hydrogen, and a C1-C6 linear, branched or cyclic alkyl group. L is a neutral ligand derived from ethylene or acetylene.

Other embodiments of the current invention may include, with out limitation, one or more of the following features:

L is bis(trimethylsilyl)acetylene;

the metal containing film is deposited onto at least one substrate at a temperature between about 70° C. and about 450° C.; preferably between about 70° C. and about 200° C.;

the metal containing film is deposited, through a plasma enhanced ALD process, at a temperature between about 50° C. and about 200° C., preferably between about 50° C. and about 150° C.;

a second precursor is introduced into the reactor, wherein the second precursor is one of Ag, Au, Cu, Ru, Mg, Ca, Zn, B, Al, In, lanthanides (including Sc, Y, La and rare earths), Si, Ge, Sn, Ti, Zr, Hf, V, Nb, and Ta; and preferably one of Ag, Au, Cu, Ru and Ta;

at least one inert fluid (e.g. N2, Ar, He, etc) and a reaction fluid are provided, the reaction fluid being either hydrogen or a reducing fluid;

the metal containing precursor is reacted with the reaction fluid;

the reaction fluid is one of $H_2$, $H_2O$, $H_2O_2$, $N_2$, $NH_3$, hydrazine and its alkyl or aryl derivatives, diethylsilane, trisilylamine, silane, disilane, phenylsilane, a molecule containing Si—H bonds, dimethylaluminum hydride, hydrogen-containing radicals such as H., OH., N., NH., $NH_2$., CO, $Si_2Cl_6$, and mixtures thereof;

the pressure in the reactor is between about 1 Pa and about 100,000 Pa; and preferably between about 25 Pa and about 1000 Pa;

metal containing precursor, the inert fluid, and the reaction fluid are either introduced at least partially simultaneously as in a chemical vapor deposition process, or are introduced at least partially sequentially as in an atomic layer deposition process;

the metal containing precursor has a melting point less than about 50 C; preferably less than about 35° C.; and the metal containing precursor is a liquid at room temperature.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

Notation and Nomenclature

Certain terms are used throughout the following description and claims to refer to particular system components. This document does not intend to distinguish between components that differ in name but not function.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation, "Me," refers to a methyl group; the abbreviation, "Et," refers to an ethyl group; the abbreviation, "Pr," refers to a propyl group; the abbreviation, "iPr," refers to an isopropyl group; the abbreviation "acac" refers to acetylacetonato; the abbreviation "tmhd" refers to 2,2,6,6-tetramethyl-3,5-heptadionato; the abbreviation "od" refers to 2,4-octadionato; the abbreviation "mhd" refers to 2-methyl-3,5-hexadinonato; and the abbreviation "tmshd" refers to 2,2,6,6-tetramethyl-2-sila-heptadionato.

DESCRIPTION OF PREFERRED EMBODIMENTS

In an embodiment, a precursor compound comprises a precursor with the general formula:

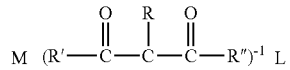

M is one of copper, silver or gold. R, R', and R" are selected from hydrogen, a C1-C6 linear, branched or cyclic alkyl group, NO2, $SiR^1R^2R^3$; and $GeR^1R^2R^3$. $R^1$, $R^2$, $R^3$ are independently selected from hydrogen, and a C1-C6 linear, branched or cyclic alkyl group. L is a neutral ligand derived from ethylene or acetylene.

Examples of the disclosed precursors containing Cu include without limitation Cu(acac)(ethylene), Cu(tmhd)(ethylene), Cu(od)(ethylene), Cu(mhd)(ethylene), Cu(acac)(propylene), Cu(tmhd)(propylene), Cu(od)(propylene), Cu(mhd)(propylene), Cu(acac)(1-butene), Cu(tmhd)(1-butene), Cu(od)(1-butene), Cu(mhd)(1-butene), Cu(acac)(2-butene), Cu(tmhd)(2-butene), Cu(od)(2-butene), Cu(mhd)(2-butene), Cu(acac)(butadiene), Cu(tmhd)(butadiene), Cu(od)

(butadiene), Cu(mhd)(butadiene), Cu(acac)(cyclobutadiene), Cu(tmhd)(cyclobutadiene), Cu(od)(cyclobutadiene), Cu(mhd)(cyclobutadiene), Cu(acac)(cyclohexa-1,3-ene), Cu(tmhd)(cyclohexa-1,3-diene), Cu(od)(cyclohexa-1,3-diene), Cu(mhd)(cyclohexa-1,3-diene), Cu(acac)(cyclohexa-1,4-diene), Cu(tmhd)(cyclohexa-1,4-diene), Cu(od)(cyclohexa-1,4-diene), Cu(mhd)(cyclohexa-1,4-diene), Cu(acac)(acetylene), Cu(tmhd)(acetylene), Cu(od)(acetylene), Cu(mhd)(acetylene), Cu(acac)(trimethylsilylacetylene), Cu(tmhd)(trimethylsilylacetylene), Cu(od)(trimethylsilylacetylene), Cu(mhd)(trimethylsilylacetylene), Cu(acac)(bis(trimethylsilyl)acetylene), Cu(tmhd)bis(trimethylsilylacetylene), Cu(od)(bis(trimethylsilyl)acetylene), Cu(mhd)(bis(trimethylsilyl)acetylene), Cu(acac)(trimethylvinylsilane), Cu(tmhd)(trimethylvinylsilane), Cu(od)(trimethylvinylsilane), Cu(mhd)(trimethylvinylsilane), Cu(acac)(bis(trimethylsilyl)acetylene), Cu(tmhd)(bis(trimethylsilyl)ethylene), Cu(od)(bis(trimethylsilyl)ethylene), Cu(mhd)(bis(trimethylsilyl)ethylene), Cu(tmshd)(propylene), Cu(tmshd)(1-butylene), Cu(tmshd)(2-butylene), Cu(tmshd)(butadiene), Cu(tmshd)(cyclobutadiene), Cu(tmshd)(cyclohexa-1,3-diene), Cu(tmshd)(cyclohexa-1,4-diene), Cu(tmshd)(acetylene), Cu(tmshd)(trimethylsilylacetylene), Cu(tmshd)(bis(trimethylsilyl)acetylene), and mixtures thereof.

Examples of the disclosed precursors containing Ag include without limitation Ag(acac)(ethylene), Ag(tmhd)(ethylene), Ag(od)(ethylene), Ag(mhd)(ethylene), Ag(acac)(propylene), Ag(tmhd)(propylene), Ag(od)(propylene), Ag(mhd)(propylene), Ag(acac)(1-butene), Ag(tmhd)(1-butene), Ag(od)(1-butene), Ag(mhd)(2-butene), Ag(acac)(2-butene), Ag(tmhd)(2-butene), Ag(od)(2-butene), Ag(mhd)(2-butaene), Ag(acac)(butadiene), Ag(tmhd)(butadiene), Ag(od)(butadiene), Ag(mhd)(butadiene), Ag(acac)(cyclobutadiene), Ag(tmhd)(cyclobutadiene), Ag(od)(cyclobutadiene), Ag(mhd)(cyclobutadiene), Ag(acac)(cyclohexa-1,3-diene), Ag(tmhd)(cyclohexa-1,3-diene), Ag(od)(cyclohexa-1,3-diene), Ag(mhd)(cyclohexa-1,3-diene), Ag(acac)(cyclohexa-1,4-diene), Ag(tmhd)(cyclohexa-1,4-diene), Ag(od)(cyclohexa-1,4-diene), Ag(mhd)(cyclohexa-1,4-diene), Ag(acac)(acetylene), Ag(tmhd)(acetylene), Ag(od)(acetylene), Ag(mhd)(acetylene), Ag(acac)(trimethylsilylacetylene), Ag(tmhd)(trimethylsilylacetylene), Ag(od)(trimethylsilylacetylene), Ag(mhd)(trimethylsilylacetylene), Ag(acac)(bis(trimethylsilyl)acetylene), Ag(tmhd)(bis(trimethylsilyl)ethylene), Ag(od)(bis(trimethylsilyl)acetylene), Ag(mhd)(bis(trimethylsilyl)acetylene), Ag(acac)(trimethylvinylsilane), Ag(tmhd)(trimethylvinylsilane), Ag(od)(trimethylvinylsilane), Ag(mhd)(trimethylvinylsilane), Ag(acac)(bis(trimethylsilyl)acetylene), Ag(tmhd)(bis(trimethylsilyl)ethylene), Ag(od)(bis(trimethylsilyl)ethylene), Ag(mhd)(bis(trimethylsilyl)ethylene), Ag(tmshd)(propylene), Ag(tmshd)(1-butylene), Ag(tmshd)(2-butylene), Ag(tmshd)(butadiene), Ag(tmshd)(cyclobutadiene), Ag(tmshd)(cyclohexadi-1,3-ene), Ag(tmshd)(cyclohexadi-1,4-ene), Ag(tmshd)(acetylene), Ag(tmshd)(trimethylsilylacetylene), Ag(tmshd)(bis(trimethylsilyl)acetylene, and mixtures thereof.

Examples of the disclosed precursors containing Au include without limitation Au(acac)(ethylene), Au(tmhd)(ethylene), Au(od)(ethylene), Au(mhd)(ethylene), Au(acac)(propylene), Au(tmhd)(propylene), Au(od)(propylene), Au(mhd)(propylene), Au(acac)(1-butene), Au(tmhd)(1-butene), Au(od)(1-butene), Au(mhd)(2-butene), Au(acac)(2-butene), Au(tmhd)(2-butene), Au(od)(2-butene), Au(mhd)(2-butaene), Au(acac)(butadiene), Au(tmhd)(butadiene), Au(od)(butadiene), Au(mhd)(butadiene), Au(acac)(cyclobutadiene), Au(tmhd)(cyclobutadiene), Au(od)(cyclobutadiene), Au(mhd)(cyclobutadiene), Au(acac)(cyclohexa-1,3-diene), Au(tmhd)(cyclohexa-1,3-diene), Au(od)(cyclohexa-1,3-diene), Au(mhd)(cyclohexa-1,3-diene), Au(acac)(cyclohexa-1,4-diene), Au(tmhd)(cyclohexa-1,4-diene), Au(od)(cyclohexa-1,4-diene), Au(mhd)(cyclohexa-1,4-diene), Au(acac)(acetylene), Au(tmhd)(acetylene), Au(od)(acetylene), Au(mhd)(acetylene), Au(acac)(trimethylsilylacetylene), Au(tmhd)(trimethylsilylacetylene), Au(od)(trimethylsilylacetylene), Au(mhd)(trimethylsilylacetylene), Au(acac)(bis(trimethylsilyl)acetylene), Au(tmhd)(bis(trimethylsilyl)ethylene), Au(od)(bis(trimethylsilyl)acetylene), Au(mhd)(bis(trimethylsilyl)acetylene), Au(acac)(trimethylvinylsilane), Au(tmhd)(trimethylvinylsilane), Au(od)(trimethylvinylsilane), Au(mhd)(trimethylvinylsilane), Au(acac)(bis(trimethylsilyl)acetylene), Au(tmhd)(bis(trimethylsilyl)ethylene), Au(od)(bis(trimethylsilyl)ethylene), Au(mhd)(bis(trimethylsilyl)ethylene), Au(tmshd)(ethylene), Au(tmshd)(propylene), Au(tmshd)(1-butylene), Au(tmshd)(2-butylene), Au(tmshd)(butadiene), Au(tmshd)(cyclobutadiene), Au(tmshd)(cyclohexadi-1,3-ene), Au(tmshd)(cyclohexadi-1,4-ene), Au(tmshd)(acetylene), Au(tmshd)(trimethylsilylacetylene), Au(tmshd)(bis(trimethylsilyl)acetylene), and mixtures thereof.

The disclosed precursor compounds may be deposited using any deposition methods known to those of skill in the art. Examples of suitable deposition methods include without limitation, conventional CVD, low pressure chemical vapor deposition (LPCVD), atomic layer deposition (ALD), pulsed chemical vapor deposition (P-CVD), plasma enhanced atomic layer deposition (PE-ALD), or combinations thereof. In an embodiment, a first precursor (i.e. the metal containing precursor) may be introduced into a reaction chamber. The reaction chamber may be any enclosure or chamber within a device in which deposition methods take place such as without limitation, a cold-wall type reactor, a hot-wall type reactor, a single-wafer reactor, a multi-wafer reactor, or other types of deposition systems under conditions suitable to cause the precursors to react and form the layers. The first precursor may be introduced into the reaction chamber by bubbling an inert gas (e.g. $N_2$, He, Ar, etc.) into the precursor and providing the inert gas plus precursor mixture to the reactor.

Generally, the reaction chamber contains one or more substrates on to which the metal layers or films will be deposited. The one or more substrates may be any suitable substrate used in semiconductor manufacturing. Examples of suitable substrates include without limitation, silicon substrates, silica substrates, silicon nitride substrates, silicon oxy nitride substrates, tungsten substrates, or combinations thereof. Additionally, substrates comprising tungsten or noble metals (e.g. platinum, palladium, rhodium or gold) may be used.

In an embodiment, a method of depositing a metal film on substrate may further comprise introducing a second precursor into the reaction chamber. The second precursor may be a metal precursor containing one or more metals other than a Group 11 metal. For example, the second precursor may include without limitation, Mg, Ca, Zn, B, Al, In, Si, Ge, Sn, Ti, Zr, Hf, V, Nb, Ta, or combinations thereof. Other examples of metals include rare earth metals and lanthanides. The second precursor may contain silicon and/or germanium. In particular, examples of suitable second metal precursors include without limitation, trisilylamine, silane, disilane, trisilane, bis(tertiary-butylamino)silane (BTBAS), bis(diethylamino)silane (BDEAS), or combinations thereof. In addition, the second metal precursor may be an aminosilane having the formula: $SiH_x(NR^1R^2)_{4-x}$. The subscript, x, is an integer between 0 and 4. $R^1$ and $R^2$ may each independently be a hydrogen group or a C1-C6 alkyl group, either linear, branched, or cyclic. $R^1$ and $R^2$ may be the same or different from on another. In one embodiment, the second metal precursor is tris(diethylamino)silane (TriDMAS).

In an alternative embodiment, the second precursor may be an aluminum source. Examples of suitable aluminum sources include without limitation, trimethylaluminum, dimethylaluminum hydride, or combinations thereof. Additionally, the aluminum source may be an amidoalane having the formula: $AlR^1{}_x(NR^2R^3)_{3-x}$. The subscript, x, is an integer from 0 and 3. $R^1$, $R^2$, and $R^3$ may each independently be a hydrogen group or a C1-C6 carbon chain, either linear, branched or cyclic and may each be the same or different from on another.

In another embodiment, the second precursor may be a tantalum and/or niobium source selected from the group comprising $MCl_5$ and corresponding adducts, $M(NMe_2)_5$, $M(NEt_2)_4$, $M(NEt_2)_5$, or combinations thereof. M represents either tantalum or niobium. Furthermore, the tantalum and/or niobium source may be an amino-containing tantalum and/or niobium source having the formula: $M(=NR^1)(NR^2R^3)_3$. $R^1$, $R^2$, and $R^3$ may each independently be a hydrogen group or a C1-C6 alkyl group, either linear, branched, or cyclic. Generally, the weight ratio of the first metal precursor to the second precursor introduced into the reaction chamber may range from about 100:1 to about 1:100, alternatively from about 50:1 to about 1:50, alternatively from about 1:1 to about 10:1.

In embodiments, the reaction chamber may be maintained at a pressure ranging from about 1 Pa to about 100,000 Pa, alternatively from about 10 Pa to about 10,000 Pa, alternatively from about 25 Pa to about 1000 Pa. In addition, the temperature within the reaction chamber may range from about 70° C. to about 450° C., alternatively from about 70° C. to about 200° C. In some embodiments, the first precursor has a melting point below about 50° C., preferably below about 35° C. In some embodiments, the first precursor is a liquid at room temperature.

Furthermore, the deposition of the metal film may take place in the presence of a hydrogen source. Thus, a hydrogen source may be introduced into the reaction chamber. The hydrogen source may be a fluid or a gas. Examples of suitable hydrogen sources include without limitation, $H_2$, $H_2O$, $H_2O_2$, $N_2$, $NH_3$, hydrazine and its alkyl or aryl derivatives, diethylsilane, trisilylamine, silane, disilane, phenylsilane and any molecule containing Si—H bonds, dimethylaluminum hydride, hydrogen-containing radicals such as H., OH., N., NH., $NH_2$., or combinations thereof. In further embodiments, an inert gas may be introduced into the reaction chamber. Examples of inert gases include without limitation, He, Ar, Ne, or combinations thereof. A reducing fluid may also be introduced in to the reaction chamber. Examples of suitable reducing fluids include without limitation, carbon monoxide, $Si_2Cl_6$, or combinations thereof.

The metal precursor and the reaction gas may be introduced sequentially (as in ALD) or simultaneously (as in CVD) into the reaction chamber. In one embodiment, the first and second precursors, or the first precursor and the reaction gas, may be pulsed sequentially or simultaneously (e.g. pulsed CVD) into the reaction chamber. Each pulse of the second and/or first metal precursor and may last for a time period ranging from about 0.01 s to about 10 s, alternatively from about 0.3 s to about 3 s, alternatively from about 0.5 s to about 2 s. In another embodiment, the reaction gas, and/or the inert gas may also be pulsed into the reaction chamber. In such embodiments, the pulse of each gas may last for a time period ranging from about 0.01 s to about 10 s, alternatively from about 0.3 s to about 3 s, alternatively from about 0.5 s to about 2 s.

EXAMPLES

The following non-limiting examples are provided to further illustrate embodiments of the invention. However, the examples are not intended to be all inclusive and are not intended to limit the scope of the inventions described herein. The following examples illustrate possible deposition methods, according to embodiments of the current invention.

Example I

Deposition of Copper Metal in CVD Conditions

In some embodiments, to make the deposition of a copper film on the surface of a wafer or in a deep trench, one need to vaporize the copper source according to an embodiment of the current invention, and provide it into a reactor in which at least one substrate was introduced, possibly inject an hydrogen source, preferably hydrogen, moisture or ammonia into said reactor, react or self-decompose the molecules at appropriate temperature (preferably between 200° C. and 450° C.) and pressure (preferably between 25 Pa and 1000 Pa) for the duration necessary to achieve either a thin film deposition on the substrate or to fill out trenches.

Example II

Deposition of Copper Metal in ALD Conditions

In some embodiments, to make the deposition of a copper film on the surface of a wafer or in a deep trench, one need to vaporize a copper source according to an embodiment of the current invention, and provide it into a reactor in which at least one substrate was introduced, inject an hydrogen source, preferably hydrogen, moisture or ammonia into said reactor which contains at least one wafer, react the molecules at appropriate temperature (preferably between 110° C. and 200° C.) and pressure (preferably between 25 Pa and 1000 Pa) for the duration necessary to achieve either a thin film deposition on the substrate or to fill out trenches. More specifically, a cycle is started when a Cu source is introduced for the pulse time duration, then the Cu source is purged out of the reactor to remove the Cu molecules which were not chemisorbed. The hydrogen source is then introduced to reduce the Cu molecules adsorbed on the wafer surface, hence forming a Cu layer. The hydrogen source is then purged to complete the cycle. The number of cycles is set to obtain the desired thickness of copper film.

Example III

Deposition of Copper Metal in Pulsed CVD Conditions

In some embodiments, to make the deposition of such film on the surface of a wafer or in a deep trench, one need to vaporize a copper source according to an embodiment of the current invention, and provide it into a reactor in which at least one substrate was introduced, inject an hydrogen source, preferably hydrogen, moisture or ammonia into said reactor which contains at least one wafer, react the molecules at appropriate temperature (preferably between 110° C. and 250° C.) and pressure (preferably between 25 Pa and 1000 Pa)

for the duration necessary to achieve either a thin film deposition on the substrate or to fill out trenches. More specifically, a Cu source is introduced for the pulse time duration. The hydrogen source is continuously introduced to reduce the Cu molecules, hence forming a Cu layer. The number of cycles is set to obtain the desired thickness of copper film.

Example IV

Deposition of Copper Metal in PEALD Conditions

In some embodiments, to make the deposition of such film on the surface of a substrate or in a deep trench, one need to vaporize a copper source according to an embodiment of the current invention, and provide it into a reactor in which at least one substrate was introduced, inject an hydrogen source, preferably hydrogen, moisture or ammonia into said reactor which contains at least one wafer, react the molecules at appropriate temperature (preferably between 50° C. and 150° C.) and pressure (preferably between 25 Pa and 1000 Pa) for the duration necessary to achieve either a thin film deposition on the substrate or to fill out trenches. More specifically, a Cu source is introduced for the pulse time duration. The hydrogen source is continuously introduced but in these process conditions, the hydrogen source has insufficient reactivity to reduce the Cu molecules. A plasma is therefore switched on to activate the hydrogen source making it very reactive, and enable to reduce the Cu molecules chemisorbed on the surface. When the plasma is switched off, the cycle is completed as the activated hydrogen source has a very short lifetime. This allows a shorter lifetime and then a higher throughput in manufacturing conditions. A layer of Cu is formed. The number of cycles is set to obtain the desired thickness of copper film.

Example V

Deposition of Copper Films

In some embodiments, all the information given in Examples I-IV is applicable in this Example V. The invention is directed to the deposition of metallic copper films onto a support such as a wafer, in a reactor using ALD, PEALD, CVD, MOCVD, pulse CVD processes.

Example VI

Deposition of Copper Alloy Film

All the information given in Example I-IV is applicable in this Example VI, except that a second M metal source is additionally provided. A second M containing precursor may also introduced into the reactor along with the M source of metal. This M containing precursor source is preferably selected from:
a) a silicon (or germanium) source and is selected from, but not limited to, the group consisting of trisilylamine, silane, disilane, trisilane, an aminosilane $SiH_x(NR^1R^2)_{4-x}$ (where x is comprised between 0 and 4; $R^1$ and $R^2$ are independently H or a C1-C6 carbon chain, either linear, branched or cyclic; preferably TriDMAS $SiH(NMe_2)_3$; BTBAS $SiH_2(NHtBu)_2$); BDEAS $SiH_2(NEt_2)_2$) and mixtures thereof (or their germanium equivalent); or
b) an aluminum source selected from the group comprising trimethylaluminum, dimethylaluminum hydride, an amidoalane $AlR^i_x(NR'R'')_{3-x}$ (where x is comprised between 0 and 4; $R^1$ and $R^2$ are independently H or a C1-C6 carbon chain, either linear, branched or cyclic) and mixtures thereof; or
c) a tantalum (or niobium) source selected from the group comprising $TaCl_5$ and corresponding adducts, $Ta(NMe_2)_5$, $Ta(NEt_2)_4$, $Ta(NEt_2)_5$, $Ta(=NR^1)(NR^2R^3)_3$ (each $R^1$ and $R^2$ are independently H or a C1-C6 carbon chain, either linear, branched or cyclic and where the amino ligand can have different substituent) and mixtures thereof; or their niobium counterparts.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:

1. A method for depositing a metal containing film on to one or more substrates with a plasma enhanced atomic layer deposition process, comprising:
a) providing at least one substrate into a reactor;
b) introducing at least one metal containing precursor into the reactor, wherein the metal containing precursor is selected from the group consisting of M(acac)(acetylene), M(tmhd)(acetylene), M(od)(acetylene), M(mhd)(acetylene), M(tmshd)(acetylene), M(acac)(trimethylsilylacetylene), M(tmhd)(trimethylsilylacetylene), M(od)(trimethylsilylacetylene), M(mhd)(trimethylsilylacetylene), M(tmshd)(trimethylsilylacetylene), M(acac)(bis(trimethylsilyl)acetylene), M(tmhd)(bis(trimethylsilyl)acetylene), M(od)(bis(trimethylsilyl)acetylene), M(mhd)(bis(trimethylsilyl)acetylene), and M(tmshd)(bis(trimethylsilyl)acetylene), and combinations thereof,
wherein:
M is a metal selected silver or gold;
c) providing at least one inert fluid and a reaction fluid into said reactor, wherein said reaction fluid is a hydrogen containing or a reducing fluid;
d) providing a plasma source, and sequentially activating and deactivating the plasma source after the introduction of the metal containing precursor;
e) reacting the metal containing precursor with the reaction fluid; and
f) depositing at least part of the metal containing precursor to form a metal containing film, pure metal or alloy, on the one or more substrates.

2. The method of claim 1, wherein steps (b) through (f) are repeated until a desired thickness of film is obtained.

3. The method of claim 1, further comprising depositing the metal containing film onto the at least one substrate at a temperature between about 200° C. and about 50° C.

4. The method of claim 3, further comprising depositing the metal containing film onto the at least one substrate at a temperature between about 150° C. and about 50° C.

5. The method of claim 1, wherein the reaction fluid comprises at least one hydrogen containing member selected from the group consisting of $H_2$, $H_2O$, $H_2O_2$, $N_2$, $NH_3$, hydrazine and its alkyl or aryl derivatives, diethylsilane, trisilylamine, silane, disilane, phenylsilane, a molecule containing Si—H bonds, dimethylaluminum hydride, hydrogen-containing radicals such as H., OH., N., NH., $NH_2$., and mixtures thereof.

6. The method of claim 1, wherein the reaction fluid is a reducing fluid selected from CO and $Si_2Cl_6$.

7. The method of claim 1, wherein the pressure in the reactor is between about 1 Pa and about 100,000 Pa.

8. The method of claim 7, wherein the pressure is between about 25 Pa and about 1000 Pa.

9. The method of claim 1, wherein the metal containing precursor has a melting point of less than about 50° C.

10. The method of claim 9, wherein the metal containing precursor has a melting point of less than about 35° C.

11. The method of claim 9, wherein the metal containing precursor is a liquid at room temperature.

12. The method of claim 1, further comprising introducing a second precursor into the reactor, wherein the second precursor comprises at least one member selected from the group consisting of: Ag, Au, Cu, Ru, Mg, Ca, Zn, B, Al, In, lanthanides (including Sc, Y, La and rare earths), Si, Ge, Sn, Ti, Zr, Hf, V, Nb, and Ta.

13. The method of claim 12, wherein the second precursor comprises at least one member selected from the group consisting of: Ag, Au, Cu, Ru, and Ta.

\* \* \* \* \*